US00PP22474P2

(12) United States Plant Patent
Catt

(10) Patent No.: US PP22,474 P2
(45) Date of Patent: Jan. 31, 2012

(54) *CARYOPTERIS* PLANT NAMED 'LISSILV'

(50) Latin Name: *Caryopteris×clandonensis*
Varietal Denomination: LISSILV

(76) Inventor: Peter Catt, Liss (GB)

( * ) Notice: Subject to any disclaimer, the term of this patent is extended or adjusted under 35 U.S.C. 154(b) by 9 days.

(21) Appl. No.: 12/806,379

(22) Filed: Aug. 10, 2010

Related U.S. Application Data

(60) Provisional application No. 61/274,316, filed on Aug. 17, 2009.

(51) Int. Cl.
*A01H 5/00* (2006.01)

(52) U.S. Cl. ..... Plt./226
(58) Field of Classification Search ..... Plt./226
See application file for complete search history.

(56) References Cited

OTHER PUBLICATIONS

UPOV-ROM GTITM, Plant Variety Database, 2011,/01, GTI Jouve Retrieval Software, Citation for plant 'LISSILV'.*

* cited by examiner

*Primary Examiner* — Susan McCormick Ewoldt

(57) ABSTRACT

A new and distinct cultivar of *Caryopteris* named 'LISSILV' that is characterized by upright habit, pronounced silver foliage color, and a prolific display of soft violet-blue flowers. In combination these traits set 'LISSILV' apart from all other existing varieties of *Caryopteris* known to the inventor.

2 Drawing Sheets

Genus: *CARYOPTERIS.*
Species: *×clandonensis.*
Denomination: 'LISSILV'.

BACKGROUND OF THE INVENTION

The present invention relates to a new variety of bluebeard, a perennial shrub grown for use in borders, landscape, and as a specimen plant. The new invention from the family Verbenaceae is known botanically as *CARYOPTERIS×clandonensis* and will be referred to hereinafter by the cultivar name 'LISSILV'.

'LISSILV' was discovered in 2006 as a chance seedling derived from the open cross-pollination of the seed parent an individual *Caryopteris clandonensis* 'Longwood Blue' (unpatented) and the pollen parent an individual *Caryopteris clandonensis* 'Heavenly Blue' (unpatented). The inventor discovered 'LISSILV' at the inventor's nursery in Greatham, Hants, United Kingdom.

The distinguishing traits of 'LISSILV' are upright habit, tidy round form, pronounced silver foliage color, and prolific display of soft violet-blue flowers that bloom summer through fall. 'LISSILV' is highly frost tolerant surviving temperatures of minus 20° Centigrade and hardy to USDA Zone 6b. 'LISSILV' grows to 90 cm. in height and 46 cm. in width at maturity. Cultural needs include full sun, rich fertile well-draining soil, and minimal to moderate water. Susceptibility to pests is similar to the species, and there are no diseases known to the inventor.

The closest comparison plant is *Caryopteris clandonensis* 'Longwood Blue'. 'LISSILV' is less vigorous than 'Longwood Blue' and grows with a more upright habit. 'LISSILV' is distinguishable from both parents by silver foliage color. 'LISSILV' exhibits lighter blue flower color and is less vigorous than 'Heavenly Blue'.

The first asexual reproduction of 'LISSILV' was conducted at the inventor's nursery in Hampshire, United Kingdom. The inventor carried out the first asexual propagation in August 2006. The method used was vegetative cuttings, taken with and without nodes then placed under intermittent mist with a base heat of 18° Centigrade. Since that time, under careful observation 'LISSILV' has been determined fixed, stable and true to type in subsequent generations of asexual propagation.

The inventor made an application for a grant of European Community Plant Breeders' Rights for 'LISSILV' having filing date Mar. 25, 2008 and serial number 2008/0659. No claim of priority is made with respect to this Plant Breeders' Rights application. All plants of 'LISSILV' remained under the inventor's control at the inventor's nursery until plants of 'LISSILV' were first displayed and first advertised for future sale to the trade and the public at the Plantarium Show in Boskoop, The Netherlands from Aug. 27, 2008.

SUMMARY OF THE INVENTION

The following traits have been repeatedly observed and represent the distinguishing characteristics of 'LISSILV'. These traits in combination distinguish 'LISSILV' from all other existing varieties of *Caryopteris* known to the inventor. 'LISSILV' has not been tested under all possible conditions. Phenotypic differences may be observed with variations in environmental, climatic, and cultural conditions without however any variance in genotype.

1. 'LISSILV' exhibits upright habit.
2. 'LISSILV' exhibits tidy rounded form.
3. 'LISSILV' exhibits pronounced silver foliage color.
4. 'LISSILV' exhibits soft violet-blue flowers summer through fall.
5. 'LISSILV' exhibits aromatic stems and foliage.
6. 'LISSILV' reaches 90 cm. in height and 46 cm. in width at maturity.
7. 'LISSILV' is frost tolerant and hardy to USDA Zone 6b.

BRIEF DESCRIPTION OF THE DRAWINGS

The accompanying color drawings illustrate the overall appearance of 'LISSILV' showing color as true as is reasonably possible to obtain in color reproductions of this type. Drawings were made of 18-month-old plants growing in the open ground in Hampshire, United Kingdom. Color in the drawings may differ from color values cited in the detailed botanical description, which accurately describe the actual color of 'LISSILV'.

Drawing labeled

Drawing labeled

Figure 1:
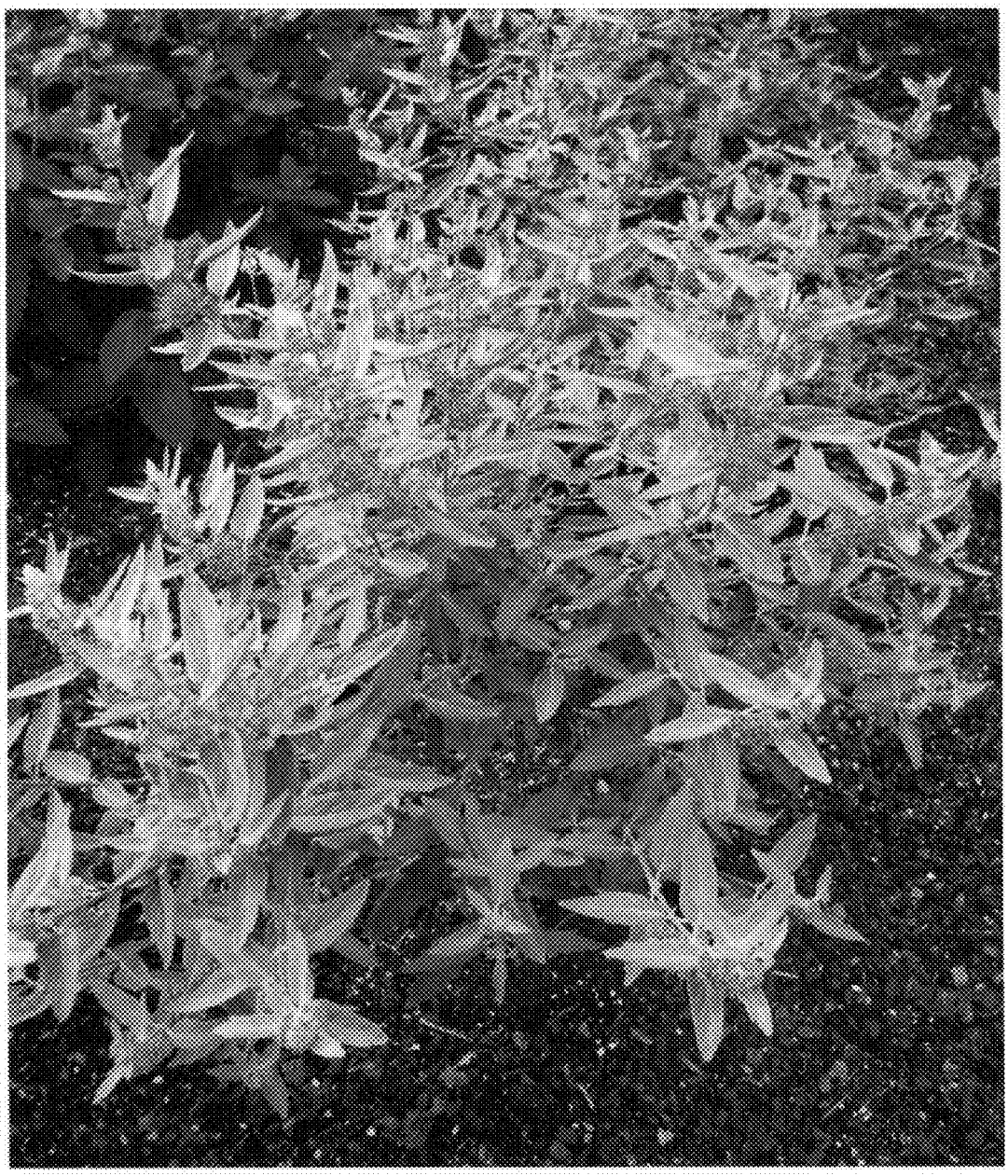
FIG. 1 depicts a side view of the plant illustrating habit, foliage, and flower color.
Figure 2:
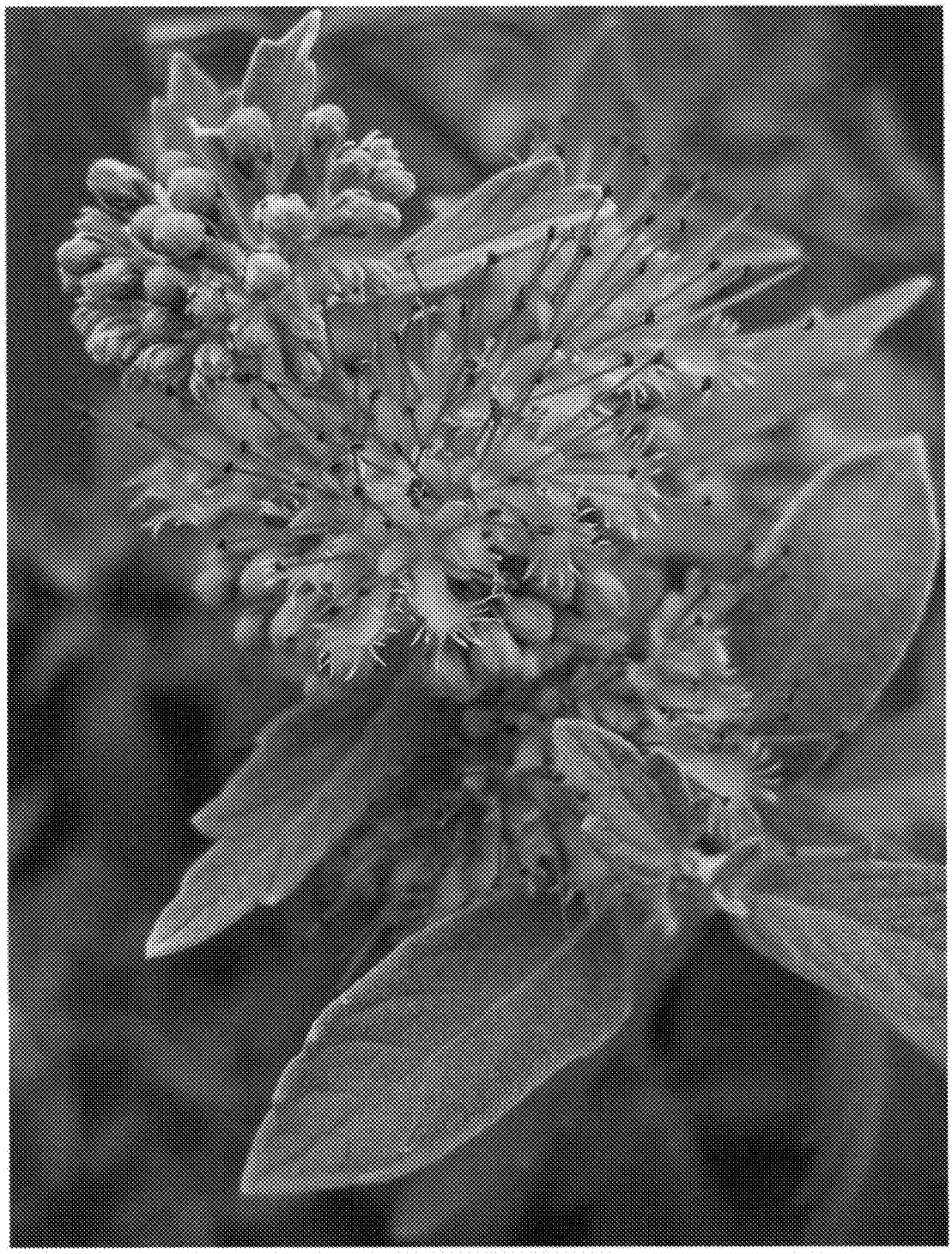
FIG. 2 depicts a close-up view of flowers and buds.

Both drawings were made using conventional techniques and although flower and foliage color may appear different from actual color due to light reflectance, they are as accurate as possible by conventional photography.

BOTANICAL DESCRIPTION OF THE PLANT

The following is a detailed botanical description of 'LISSILV'. Observations, measurements, values and comparisons were collected in September from 2-liter container plants grown out-of-doors in Arroyo Grande, Calif. Color determinations are made in accordance with The 2001 Royal Horticultural Society Colour Chart from London, England, except where general color terms of ordinary dictionary significance are used. The growing requirements of 'LISSILV' are similar to the species.

Botanical classification: *CARYOPTERIS*×*clandonensis* 'LISSILV'.
Family: Verbenaceae.
Genus: *CARYOPTERIS*.
Species: ×*clandonensis*.
Denomination: 'LISSILV'.
Common name: Bluebeard.
Habit: Upright.
Form: Round and tidy.
Commercial category: Perennial shrub.
Use: Suitable for border, landscape, and specimen plant.
Suggested commercial container size: 1-liter container and larger.
Parentage:
- *Seed parent.*—*Caryopteris clandonensis* 'Longwood Blue'.
- *Pollen parent.*—*Caryopteris clandonensis* 'Heavenly Blue'.

Propagation method: Vegetative cuttings with or without nodes kept under intermittent mist with a base heat of 18° Centigrade.
Rooting system: Fine.
Vigor: Minimal to moderate.
Crop time (average): 22 months to produce a 1.3-liter container from stem cuttings.
Mature height (average): 90 cm.
Mature width (average): 46 cm.
Cultural requirements: Performs best in full sun, with rich fertile free-draining soil, and minimal to moderate water.
Disease and pest susceptibility: Same as species.
Disease and pest resistance: None known to the inventor.
Hardiness: USDA Zone 6b.
Special considerations: Can tolerate pronounced frost. Provide some heat mid-February.
Stem:
- *Branching habit.*—Basal and free lateral branching.
- *Lateral branch quantity* (*range*).—35-40 per 1-liter container plant.
- *Shape.*—Obcylindric.
- *Surface.*—Pubescent.
- *Stem appearance.*—Iridescent.
- *Color.*—N199B.
- *Stem length* (*average*).—15 cm.
- *Stem diameter* (*average*).—3 mm.
- *Stem strength.*—Brittle.
- *Internode* (*average*).—3.50 cm.
- *Stem fragrance.*—Resinous scent.

Foliage:
- *Type.*—Deciduous.
- *Leaf arrangement.*—Opposite.
- *Leaf division.*—Simple.
- *Leaf quantity* (*average*).—20 per lateral stem.
- *Leaf margin* (*range*).—Sub-entire to slightly dentate.
- *Leaf surface* (*abaxial and adaxial*).—Densely pubescent.
- *Pubescence color.*—188D.
- *Leaf texture.*—Velvety.
- *Leaf shape* (*range*).—Ovate to oblanceolate.
- *Leaf length* (*range*).—2.50-5 cm.
- *Leaf width* (*average*).—1.70 cm.
- *Leaf color* (*abaxial surface*).—190A.
- *Leaf color* (*adaxial surface*).—189A.
- *Venation pattern.*—Pinnate.
- *Vein color* (*abaxial surface*).—191B.
- *Vein color* (*adaxial surface*).—191A.
- *Leaf apex.*—Acute.
- *Leaf base.*—Rounded.
- *Attachment.*—Petiolate.
- *Petiole surface.*—Pubescent.
- *Petiole shape.*—Sulcate.
- *Petiole color.*—189B.
- *Petiole dimensions* (*average*).—4 mm. in length and 1 mm. in diameter.
- *Durability of foliage to stress.*—Moderate.
- *Stipules.*—Present.
- *Stipule surface.*—Densely pubescent.
- *Stipule color.*—194A.
- *Stipule dimensions.*—<1 mm. in height and width.
- *Stipule shape.*—Ovate.
- *Leaf fragrance.*—Mint scented.

Inflorescence:
- *Type.*—Terminal and axial cymes.
- *Inflorescence quantity* (*average*).—75 per 1-liter container plant.
- *Inflorescence dimensions* (*average*).—2 cm. in height and 2.5 cm in width.
- *Rate of opening* (*range*).—40% of inflorescence opens in 10 days.
- *Blooming months.*—June through October.
- *Flower quantity* (*average*).—25 per inflorescence.
- *Flower dimensions.*—1.50 cm. in depth and 0.75 cm. in diameter.
- *Flower aspect.*—Upright to outward.
- *Persistent or self-cleaning.*—Self-cleaning.
- *Peduncle shape.*—Cylindrical.
- *Peduncle surface.*—Densely pubescent.
- *Peduncle strength.*—Moderate.
- *Peduncle color.*—194A.
- *Peduncle dimensions* (*average*).—6 mm. in length and 2 mm. in diameter.
- *Pedicel dimensions.*—1 mm. in length and <1 mm. in diameter.
- *Pedicel color.*—194A.
- *Pedicel strength.*—Moderate.

*Bud quantity* (*average*).—25 per inflorescence.
*Bud shape.*—Globular.
*Bud apex.*—Obtuse.
*Bud color.*—190C.
*Bud surface.*—Lanate.
*Bud dimensions.*—1.50 mm. in length and 1.50 mm. in diameter.
*Corolla shape.*—Campanulate with 5 lobes.
*Corolla dimensions.*—1 cm. in depth and 0.75 cm. in diameter.
*Corolla longevity on plant* (*average*).—12 days.
*Corolla tube dimensions.*—4 mm. in length and 2 mm. in width.
*Corolla tube color.*—N155A.
*Corolla lobe.*—5 in number.
*Corolla lobe color* (*abaxial surface*).—90C.
*Corolla lobe color* (*adaxial surface*).—90A.
*Corolla lobe surface* (*abaxial and adaxial*).—Glabrous.
*Corolla lobe length* (*range*).—3-6 mm.
*Corolla lobe width* (*range*).—2-3 mm.
*Corolla lobes fused or unfused.*—Basally fused.
*Corolla lobe margin* (*range*).—Entire to fimbriate.
*Corolla lobe shape* (*range*).—Obovate to spathulate.
*Corolla lobe apex.*—Obtuse.
*Calyx shape.*—Deep campanulate.
*Calyx color.*—188A.
*Calyx dimensions.*—5 mm. in length and 3 mm. in width.
*Sepals.*—5 in number.
*Sepal shape.*—Narrow elliptic.
*Sepal dimensions.*—5 mm. in length and <1 mm. in width.
*Sepals fused or unfused.*—Basally fused.
*Sepal color* (*abaxial and adaxial surface*).—188A.
*Sepal margin.*—Entire.
*Sepal apex.*—Acute.
*Sepal surface* (*abaxial and adaxial*).—Lanate.
*Flower fragrance.*—None observed.

Reproductive organs:
*Stamen quantity.*—4 in number.
*Stamen length.*—11 mm.
*Stamen color.*—90A.
*Anther color.*—N186A.
*Anther length.*—<1 mm.
*Pollen amount.*—Minimal.
*Pollen color.*—93A.
*Pistil quantity.*—1 in number.
*Pistil length.*—7 mm.
*Pistil color.*—91A.
*Stigma shape.*—Bifid.
*Stigma color.*—91A.
*Ovary position.*—Superior.
*Ovary color.*—146D.
*Ovary dimensions.*—1.50 mm in height and 1 mm. in width.
*Ovary shape.*—Ovoid.
*Ovary surface.*—Glabrous.

Fruit and seed: Fruit or seed have not been observed.

The invention claimed is:

1. A new and distinct cultivar of *Caryopteris* plant named 'LISSILV' as described and illustrated herein.

* * * * *